United States Patent [19]
Emerson

[11] Patent Number: 6,090,752
[45] Date of Patent: Jul. 18, 2000

[54] HERBICIDAL COMPOSITIONS

[75] Inventor: Ralph W. Emerson, Davis, Calif.

[73] Assignee: Summus Group Ltd., Woodland, Calif.

[21] Appl. No.: 09/302,051

[22] Filed: Apr. 29, 1999

Related U.S. Application Data

[60] Provisional application No. 60/083,848, May 1, 1998.

[51] Int. Cl.$^7$ ............................ A01N 37/02; A01N 37/10
[52] U.S. Cl. ......................... 504/157; 504/313; 504/314; 504/318
[58] Field of Search ..................... 504/157, 313, 504/314, 318

[56] References Cited

U.S. PATENT DOCUMENTS

| | | | |
|---|---|---|---|
| 2,394,916 | 2/1946 | Jones | 167/45 |
| 3,183,075 | 5/1965 | Walworth | 71/2.6 |
| 3,597,469 | 8/1971 | Bradwell | 260/468 P |
| 3,681,045 | 8/1972 | Gough | 71/107 |
| 3,944,411 | 3/1976 | Rohr | 71/107 |
| 3,983,214 | 9/1976 | Misato et al. | 424/180 |
| 4,388,473 | 6/1983 | Richter et al. | 560/65 |
| 4,902,334 | 2/1990 | Azuma et al. | 71/88 |
| 5,087,417 | 2/1992 | Dumbroff et al. | 422/1 |
| 5,129,951 | 7/1992 | Vaughn et al. | 71/122 |
| 5,149,715 | 9/1992 | Armstrong et al. | 514/701 |
| 5,362,705 | 11/1994 | Moucharafieh et al. | 504/206 |
| 5,411,944 | 5/1995 | Young | 504/206 |
| 5,538,940 | 7/1996 | Sauter et al. | 504/314 |
| 5,672,352 | 9/1997 | Clark et al. | 424/405 |
| 5,703,013 | 12/1997 | Caulder et al. | 504/131 |
| 5,792,467 | 8/1998 | Emerson et al. | 424/405 |
| 5,839,224 | 11/1998 | Emerson et al. | 47/58 |
| 5,843,375 | 12/1998 | Emerson et al. | 422/36 |

FOREIGN PATENT DOCUMENTS

WO 97/35471  10/1997  WIPO.

*Primary Examiner*—S. Mark Clardy
*Attorney, Agent, or Firm*—Cooley Godward LLP

[57] ABSTRACT

A method and composition for inhibiting the growth of a weed is described. The herbicidal composition comprises an agriculturally-acceptable carrier in combination with a compound of Formula (I):

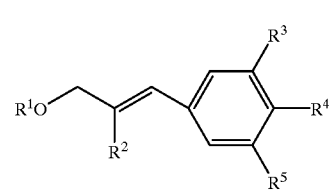

(I)

wherein $R^1$ is alkylcarbonyl or arylcarbonyl; $R^2$ is alkyl or H; $R^3$ is H, OH or alkoxy; $R^4$ is H or OH; and $R^5$ is H, OH or alkoxy.

19 Claims, No Drawings

HERBICIDAL COMPOSITIONS

CROSS REFERENCE TO RELATED APPLICATION

This application claims the benefit of U.S. Provisional Application No. 60/083,848, filed on May 1, 1998.

BACKGROUND

1. Field of the Invention

This invention relates to herbicides. More particularly, this invention relates to biorational herbicides.

2. Background of the Invention

Controlling weeds is an agricultural management issue as ancient as food crops themselves. A weed can be defined as a plant without virtue, that is, a plant growing where it is not desired. Until science brought forth modern chemical solutions, most weed control was accomplished through brute force. Today, a wide range of chemical products have been developed in an effort to control these noxious plants. Weeds are now classified as pests and the chemical term used to describe a composition that controls weeds is "herbicide".

Weeds are of enormous economic importance. As the agricultural community deals with problematic issues, such as loss of invaluable top soil and reduction of dedicated agricultural land to ever expanding suburban housing and commercial development, the economic losses to weed infestation take on ever increasing importance.

Nearly all of modern business is affected some way by matters of weed control. Through out the world, less developed and more advanced countries alike, weed infestation results in lower crop yield and can ultimately be linked to a lower standard nutritional well being, which, in turn, can translate to ill health. If food is, in a sense, considered medicine, then the loss or reduction in yield of important food crops can initiate or prolong disease in human and animal populations.

Other lesser, yet still important impacts of weed infestation include: aesthetic diminution of public recreational and home landscape areas; increased costs associated with controlling insect, arachnid, and fungal plant diseases that accompany these annoying plants; degraded and lower quality produce; increased water allocation; additional field management problems; and reduced human and machine field efficiency.

The cost of weed infestation to mankind is much higher than is generally recognized. The presence of weeds is rather ubiquitous on all of the 500+million acres of US crop land and one billion plus acres of range land. It is estimated that weeds are responsible for agricultural losses and control costs in the United States of approximately $4 billion and $7.5 billion, respectively. Worldwide impacts are more difficult to obtain, but can safely be considered of comparable magnitude. In Canada, for example, the estimated annual loss is approximately $1 billion. These estimated losses do not include the damage caused by weeds to pastures, hay crops, and range lands, or to livestock as a result of weed related phytotoxins that affect animals.

Many herbicides presently available for use may be found in the Sixth Edition of the "Herbicide Handbook of the Weed Science Society of America", published by the Weed Society of America, 309 West Clark Street, Champaign, Ill. 61820. In general, these are synthetic chemicals that do not occur in nature. Many of these non-natural herbicides have a low $LD_{50}$ value and thus are toxic to animals, particularly man. Examples of these include arsenicals (e.g., disodium methane arsenate and methylarsonic acid), substituted ureas, 2, 4-D (2, 4-dichlorophenoxy acetic acid), 2, 4-D amine, glyphosphate (N-(phosponomethyl) glycine (sold under the name ROUNDUP®, Monsanto) or its isopropylamine salt. Reports suggest that ROUNDUP® herbicide is the third most common source of pesticide-related illnesses for farm workers. The product is toxic to fish and thus is not approved for use on aquatic vegetation.

Thus, it seems clear that it is generally preferred that herbicides have minimal adverse impact on the environment, other than on the target species. It would also be preferable to provide a herbicide that is a compound that exists in nature. Under recent Environmental Protection Agency guidelines, when such naturally-occurring compounds are used as herbicides, they are termed biorational herbicides. Such compounds can then be synthesized by standard organic synthetic methods.

It is clear in light of the above disclosure, that there would exist considerable economic advantage for the development of effective biorational herbicides that could be added to the current arsenal of integrated pest management (IPM) herbicides.

Objects of the Invention

One object of this invention is to provide a new family of herbicides based on easily obtainable compounds that are 3-phenyl-2-propen-1-ol alkanoates or benzoates.

Another object of this invention is to provide a new family of herbicides using naturally-occurring compounds.

Yet another object of this invention is to provide a new family of herbicides having low toxicity to animals when used at a herbicidally effective level.

Other objects may be apparent to one of skill in the art upon reading the following specification.

SUMMARY OF THE INVENTION

One aspect of the present invention is a method for controlling weeds, such as by inhibiting weed growth. The method comprises applying to a plant part of the weed, such as foliage, an herbicidally effective amount of a composition comprising an agriculturally-acceptable carrier in combination with a compound of Formula (I):

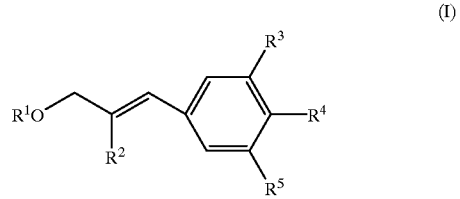

wherein $R^1$ is alkylcarbonyl, preferably $C_{1-5}$alkylcarbonyl, or arylcarbonyl; $R^2$ is alkyl, preferably $C_{1-6}$alkyl, or H; $R^3$ is H, OH or alkoxy, preferably $C_{1-4}$alkoxy; $R^4$ is H or OH; and $R^5$ is H, OH or alkoxy, preferably $C_{1-4}$alkoxy.

Another aspect of the present invention is a composition for controlling weeds, which composition comprises an agriculturally-acceptable carrier in combination with an herbicidally active compound of Formula (I).

Yet another aspect of the present invention is an article of manufacture that comprises a container in association with instructions for controlling weeds and holding a composition comprising an agriculturally-acceptable carrier and an herbicidally active compound of Formula (I).

DETAILED DESCRIPTION OF THE PREFERRED EMBODIMENTS

Herbicides are generally classified as selective or non-selective. When selective, a herbicide is used to kill weeds without harming a crop; when non-selective, it is used to kill all vegetation. Selective and non-selective materials can be applied as a function of their mode of action to the weed foliage or to the soil containing weed seeds and seedlings. Selectivity is the capacity of a herbicide, when properly applied, to be active only against certain species of plants. Selectivity can be achieved, however, also by spray placement, a method of spraying only the target weeds and not the crop plants. The compounds of the invention have herbicidal activity against one or more weed species. However, it is understood that certain compounds may be more effective on some weeds than others, and may even be ineffective against some weeds. It follows that one compound of the invention may be more selective than others. However, that does not in any way detract from their value as herbicides since the invention contemplates using some of these compounds as broad, general acting non-selective herbicides, while others have utility as specific or selective herbicides. The Examples set forth below illustrate methods by which the broad-acting or selectivity of herbicidal activity may be readily ascertained.

A weed can be defined as a plant without virtue. Accordingly, as used herein the term "weed" is intended to include all such plants whose growth, reproduction or proliferation is undesired or unwanted. These include both annual and perennial plants, for example, broadleaf plants, grasses, sages, aquatic plants, trees, and parasitic flowering plants, such as dodder, mistletoe, and witchweed. Numerous examples of weeds are set forth in the discussion and Examples.

The present invention provides very efficacious herbicides with rapid time course control of weeds. The compounds are particularly effective for controlling broad leaf plants and for grasses. In its preferred aspect, certain of the herbicides are designated as biorational. A biorational herbicide is a chemical substance of natural origin that can be synthesized. The preferred herbicides of the present invention have a lethal effect on specific targets, possessing a unique mode of action. Unlike the bulk of currently available herbicides on the agricultural market, the preferred agents have ingredients that have been proven to be substantially non-toxic to man and domestic animals and which have minimal adverse effects on wildlife and the environment.

The efficacy of the subject composition is monitored by determining its adverse effect upon treated weeds. This includes phytotoxicity or damage to the weeds, inhibition of weed growth, inhibition of weed reproduction or proliferation, or complete destruction/death of the weed, all of which are encompassed by the term "controlling". As used herein, the terms "herbicidal activity" and "herbicidally active" are intended to mean that the compound has an adverse affect on one or more weed species, i.e., is effective to control weeds. The term "herbicidally effective amount" is an amount of the compound, or a composition containing the compound, that has an adverse affect on at least 25% of the weeds treated, more preferably at least 50% of the weeds treated, and most preferably at least 70% or greater. The actual value of an herbicidally effective amount for a given compound is preferably determined in field bioassays on a plant-by-plant basis. The routine screening procedures employed to evaluate herbicidal activity and efficacy usually includes a complement of monocotyledonous and dicotyledonous test species. The viable action seen and discerned at the whole-plant level when herbicides are applied under field conditions yields a time course of herbicide action. Visible injury can be observed of the time course which includes rapid visible signs of phytotoxicity such as desiccation and epinasty. It is expected that about 0.5 to 6 pounds of the compound of the invention will be needed to treat an acre of weeds. It is expected that compounds of the invention having a higher level of herbicidal activity can be used in smaller amounts and concentrations, while those having a lower level of activity may require larger amounts or concentrations in order to achieve the same herbicidal effect. It is preferred that the compounds of the invention have minimal or no adverse effect on desired vegetation such as ornamental and agricultural plants, wildlife and humans that may come into contact with such compound or with weeds that have been treated with a composition containing such compound.

Compositions

One aspect of this invention is a composition which comprises a biorational herbicide compound and a suitable agriculturally-acceptable carrier.

The compounds useful in this invention are represented by Formula (I)

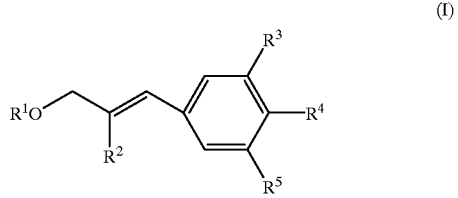

(I)

wherein $R^1$ is alkylcarbonyl, preferably $C_{1-5}$alkylcarbonyl, or arylcarbonyl;

$R^2$ is alkyl, preferably $C_{1-6}$alkyl, or H;

$R^3$ is H, OH or alkoxy, preferably $C_{1-4}$alkoxy;

$R^4$ is H or OH; and $R^5$ is H, OH or alkoxy, preferably $C_{1-4}$alkoxy.

As used herein, the term "alkyl" means a branched or unbranched saturated monovalent hydrocarbon radical containing 1 to 12 carbon atoms, such as methyl, ethyl, propyl, tert-butyl, butyl, n-hexyl, n-octyl and the like, unless otherwise indicated. Preferably the alkyl group is a lower alkyl (branched or unbranched saturated monovalent hydrocarbon radical) having 1 to 6 carbon atoms ($C_{1-6}$), such as methyl, ethyl, tert-butyl, and the like.

The term "alkoxy" means the group —O—(alkyl) wherein alkyl is as herein defined. Preferably the alkoxy group has 1 to 4 carbon atoms ($C_{1-4}$).

The terms "alkylcarbonyl" and "arylcarbonyl" refer to alkyl and aryl groups, respectively, attached through a carbonyl, —C(O)— group, and include by way of example, methyl carbonyl, ethyl carbonyl and phenyl carbonyl. Preferably the alkylcarbonyl group is a $C_{1-5}$alkylcarbonyl carbonyl group.

Compounds of interest include those set forth in Table I, where the "R" groups correspond to the "R" groups defined for formula (I). It is to be understood that the compounds shown are merely representative and not exhaustive. Others will be apparent to those of skill in the art, given this disclosure.

TABLE I

| Name | $R^1$ | $R^2$ | $R^3$ | $R^4$ | $R^5$ |
|---|---|---|---|---|---|
| cinnamyl acetate | $H_3C-C(O)-$ | H | H | H | H |
| cinnamyl benzoate | $Ph-C(O)-$ | H | H | H | H |
| α-propyl cinnamyl benzoate | $Ph-C(O)-$ | Pr | H | H | H |
| α-amyl cinnamyl acetate | $H_3C-C(O)-$ | Am | H | H | H |
| α-hexyl cinnamyl benzoate | $Ph-C(O)-$ | Hex | H | H | H |
| coniferyl acetate | $H_3C-C(O)-$ | H | $-OCH_3$ | $-OH$ | H |
| coniferyl benzoate | $Ph-C(O)-$ | H | H | H | H |
| α-amyl coniferyl acetate | $H_3C-C(O)-$ | Am | H | H | H |
| sinapyl acetate | $H_3C-C(O)-$ | H | $-OCH_3$ | $-OH$ | $-OCH_3$ |
| sinapyl benzoate | $Ph-C(O)-$ | H | $-OCH_3$ | $-OH$ | $-OCH_3$ |

The following abbreviations are used in Table I: "Pr" is n-propyl, "Hex" is n-hexyl, "Am" is amyl, and "Ph" is phenyl.

Compounds useful in the composition of this invention are available from sources known in the art, such as Aldrich Chemical Co. and Sigma Chemical Co., or are readily synthesized as are well known in the art.

Referring to Formula (I), the preferred $R^1$ substituent is $C_{1-5}$alkylcarbonyl such as methylcarbonyl, or arylcarbonyl such as phenylcarbonyl, with methylcarbonyl being more preferred. The preferred $R^2$ substituent is $C_{1-6}$alkyl such as n-propyl, n-hexyl and amyl, or H.

The preferred $R^3$ substituent is H or $C_{1-4}$alkoxy such as methoxy, most preferably H. The preferred $R^4$ substituent is H or OH, more preferably H. The preferred $R^5$ substituent is H or $C_{1-4}$alkoxy such as methoxy. Also preferred are those compounds where one or more of $R^2$, $R^3$, $R^4$ and $R^5$ are H.

Preferred compounds of Formula (I) include cinnamyl acetate, cinnamyl benzoate, α-propyl cinnamyl benzoate, α-amyl cinnamyl acetate, α-hexyl cinnamyl benzoate, coniferyl acetate, coniferyl benzoate, α-amyl coniferyl acetate, sinapyl acetate and sinapyl benzoate. Particularly preferred compounds of Formula (I) include cinnamyl acetate.

The composition may be solid (i.e., in a powdered form) or liquid depending on the carrier and the needs of the agriculturist using the composition. If the composition is solid, suitable carriers include various known, agriculturally-useful powders that are generally used for this purpose. If the composition is liquid, it may be aqueous or non-aqueous and may be a solution, suspension, or emulsion, depending on the needs of the agriculturist applying the herbicidal composition.

Generally, a composition of this invention will be prepared as a concentrate for industrial application and further dilution or as a fully diluted ready-to-apply composition. Preferably, the composition is applied as a liquid, whether aqueous or non-aqueous, but preferably the former. The concentrate, if solid, will be formulated to be mixed to form an appropriate non-aqueous or aqueous composition. Thus, the composition will generally contain the active compound along with a surfactant carrier to enough miscibility or suspendability of the composition in a liquid.

In general, the percentage by weight of the active compound, i.e., the active ingredient will be about 0.1% to 50 wt %. Higher concentrations are usually preferred for purposes of manufacture, shipment, and storage. For example, as a concentrate for use by professional agronomists the percentage will be at least about 10 wt %, preferably about 25 to 50% by weight. Prior to use, the high concentration composition is diluted in a solvent to an appropriate concentration for the intended use of the composition. When fully diluted for consumer use as a "ready for use" product, the composition will be typically be about 0.5% to 10 wt %, more preferably 1 to 5 wt %.

An antioxidant may also be included at a level sufficient to increase the product shelf life, inhibit decomposition of the active compound in the herbicidal composition, or improve the stability of the controlling effect when the composition is applied to weeds. Suitable antioxidants include, but are not limited to, ascorbyl palmitate, anoxomer, benzoic acid, benzlkonium chloride, benzethonium chloride, benzyl alcohol, butylated hydroxyanisole, butylated hydroxytoluene, chlorobutanol, dehydroacetic acid, ethylenediamine, ferulic acid, potassium benzoate, potassium metabisulfite, potassium sorbate, n-propyl gallate BP, propylparaben, sassafras oil, sodium benzoate, sodium bisulfite, sodium metabisulfite, sorbic acid, vitamin E, eugenol, and α-tocopherol and the like. The antioxidant can be present in an amount of about 0.01–10 wt %, but generally no more than about 1 wt % will be needed. A preferred amount can be determined by shelf-life stability trial according to an EPA standard protocol. A minimal amount of antioxidant which maintains the shelf stability is selected to save the cost of manufacturing.

The subject composition can be an aqueous composition using water as a solvent or an organic composition using an organic solvent, such as ether, ketone, kerosene, or alcohol. A water solvent is preferred because it mimics nature (biorational), is environmentally safe, and also costs little. The compositions of this invention, particularly liquids and soluble powders, preferably contain, as a conditioning agent, one or more surfactants in amounts sufficient to render a given composition readily dispersible in water or in an organic solvent. The incorporation of a surfactant into the compositions greatly enhances their efficiency. The water, organic solvent, or surfactant (alone or in combination with a solvent) functions as the agriculturally-acceptable carrier.

By the term "surfactant" it is understood that wetting agents, dispersing agents, suspending agents, and emulsifying agents are included therein. Anionic, cationic and non-ionic agents can be used, although non-ionic agents are preferred. The non-ionic surface-active agents include allinol, nonoxynol, octoxynol, oxycastrol, oxysorbic (for example, polyoxyethylated sorbitol fatty-acid esters (TWEEN®)); thalestol, and polyethylene glycol octylphenol ether (TRITON®). The anionic type of agents include fatty-acid salts, higher alcohol sulfuric esters and alkylallylsulfonates; the cationic type of agents include aliphatic amino salts, quaternary ammonium salts and alkylpyridinium salts, individually or in combination. Particularly suitable surfactants include, by way of illustration and not limitation, TWEEN® 20 (polyoxyethylene sorbitan monolaurate), TWEEN®40, TWEEN®80, along with TRITON®SP 150, TRITON®SP 180 and TRITON®SP190; the most preferred being TWEEN®80 and TRITON®SP190. Of these, the nonionic surfactants are preferred. Usually, the amount of surfactant used is the minimum amount required to get the compound into solution/emulsion, and will generally be 0.5 to 10% by weight, more typically 0.5 to 1%.

The common and chemical names of other generally available adjuvants include, but are not limited to, the following list, in which the first name is the common name used in the industry, the second name is the general chemical name, the third name is the class of the compound, the fourth name is the type of surfactant, with trade name is last.

Albenate: Alkyl($Cl_{18}C_{24}$)benzene sulfonic acid and its salts; Alkylaryl sulfonate; Anionic surfactant; Nacconol 88SA, Calsoft F-90, DDBSA, Santomerse No. 3.

Alfos: $\alpha$-Alkyl($C_{10}$–$C_{16}$)-$\omega$)-hydroxypoly(oxyethylene) mixture of dihydrogen phosphates esters; polyoxyethylene alkyl phosphate ester; Anionic; Emcol PS-131.

Allinate: $\alpha$-Lauryl-$\omega$-hydroxypoly(oxyethylene) sulfate; lauryl polyoxyethylene sulfate salts; Anionic; Sipon ES.

Allinol: $\alpha$-Alkyl($C_{11}$–$C_{15}$)-$\omega$-hydroxypoly(oxyethylene); $C_{11}C_{15}$ linear primary alcohol ethoxylate; Nonionic; Neodol 25-3, Alfonic 1014–40 and other alfonic materials.

Diocusate: Sodium dioctyl-sulfosuccinate; Dioctyl sodium sulfosuccinate; Anionic; TRITON GR-5, Aerosol OT.

Dooxynol: $\alpha$-(p-Dodecyl-phenyl)-$\omega$)-hydroxypoly (oxyethylene); dodecylphenol condensation with ethylene oxide; Nonionic; Igepal RC-630, Tergitol 12-P-9, Sterox D Series.

Ligsolate: Lignosulfonate, $NH_4$, Ca, Mg, K, Na, and Zn salts; Salts of lignosulfonic acids; Anionic; Marasperse N-22, Polyfon O.

Nofenate: $\alpha$-(p-Nonylphenyl)-$\omega$-hydroxypoly (oxyethelene) sulfate, $NH_4$, Ca, Mg, K, Na, Zn salts, Nonyl group is a propylene trimer isomer; Salts of sulfate ester of nonylphynoxypoly(ethyleneoxy) ethanol; Anionic; Alipal CO Series Nonfoster: $\alpha$-(p-Nonylphenyl)-$\omega$-hydroxypoly (oxyethylene); mixture of dihydrogen phosphate and nonophosphate esters; Polyoxyethylene nonylphenol phosphate esters; Anionic; Gafac RM 510.

Nonoxynol: $\alpha$-(p-Nonylphenyl)-$\omega$-hydroxypoly (oxyethylene); polyoxyalkylene nonylphenol; Nonionic; Sterox N Series, Makon 6, Igepal CO Series TRITON N Series, T-DET N.

Octoxynol: $\alpha$-[p-1,1,3,3-Tetramethyl butyl phenyl]-$\omega$-hydroxypoly(oxyethylene); polyoxyethylene octyl phenol; Nonionic; Igepal CA-630, TRITON X-100.

Oxycastol: Castor oil polyoxyethylated; Ethoxylated castor oil; Nonionic; Emulphor EL-719, Emulphor EL-620, Trylox CO-40, T-DET C-40

Oxysorbic: Polyoxyethylated sorbitol fatty acid esters (nonosterate, monoleate etc); Polyoxyethylated sorbitol fatty acid esters; Nonionic; Atlox 1045, Drewmulse POE-STS, TWEEN Series G-1045.

Tall oil: Tall oil, fatty acids not less than 58%, rosin acids not greater than 44%, unsapolifiables not greater than 8%; Tall oil; Anionic; Ariz. S.A. Agent 305.

Thalestol: Polyglyceryl phthalate ester of coconut oil fatty acid; Modified phthalic glycerol alkyl resin; Nonionic; TRITON B-1956.

The subject composition may be prepared by simply mixing together the requisite amount of at least one compound of the invention and at least one agriculturally acceptable carrier, i.e., surfactant, alone or with a solvent. Other additives, such as a saponins and antioxidants, may be included prior to mixing.

Water-dispersible powder, capsule, or pellet compositions can be made containing one or more compounds of the invention, an inert solid extender, and one or more wetting and dispersing agents. The inert solid extenders are usually of mineral origin, such as natural clays, diatomaceous earth and synthetic minerals derived from silica and the like. Examples of such extenders include kaolinites, attapulgite clay and synthetic magnesium silicate. The water-dispersible powders can also include fatty-acid esters and antioxidants.

Treatment

The subject methods apply the compositions to unwanted vegetation, i.e., weeds, during preplanting, preemergence, and postemergence, with regard to the stage of weed development or planting crops. Preplanting applications for control of unwanted vegetation are made prior to planting crops in an area containing the unwanted vegetation, usually within a few days or weeks of planting crops. Preemergence applications are completed prior to emergence of the weeds after planting of crops. Postemergence applications are made after the weed emerges from the soil. The subject methods apply the composition by broadcast applications, which cover the entire area including the crop; by spot treatments, which are confined to small areas of weeds; by directed sprays, which are applied to selected weeds or are applied to the soil to avoid contact with the crop.

The subject method provides for application of the composition to a plant part of the weeds. For example, the composition, in a liquid or dust form, can be applied directly to plant parts of the unwanted vegetation, such as foliage/leaves, trunk, stem or roots. The contacting method is most effective against annuals, those weeds that germinate from seeds and grow to maturity each year. Complete coverage of plant parts with contact materials is preferred.

The composition can also be provided to a plant part by translocation, i.e., the composition can migrate from one cell to another such as between a cell on the plant's surface to a cell beneath the surface, or between adjacent cells. The composition can also be absorbed either by roots or above-ground parts of plants and is then moved within the plant system to distant tissues. For example, contacting foliage of the unwanted vegetation with the composition translocates the composition to roots. By translocation, plant parts below the ground or water surface are killed. The translocation method is effective against all weed types. For example, the advantage is seen when used to control established perennials, those weeds that continue their growth from year to year. Uniform application is preferred for the translocated materials, whereas complete coverage with the materials is not required.

One embodiment of the subject method is to apply the subject composition to above-ground portions of plants. The application of liquid and particulate solid compositions to above-ground portions of plants can be carried out by conventional methods, e.g., power dusters, boom and hand sprayers and spray dusters. The compositions can also be applied from airplanes as a dust or a spray because of their effectiveness at low dosages. The subject method controls unwanted vegetation by application to the foliage of an effective amount of the subject composition. While very minor dosage rates of the novel compositions deter weed growth, adequate control usually involves the application of a sufficient amount to either eliminate undesired vegetation or significantly deter its growth. Dosage rates required to accomplish these effects, of course, vary depending on plant type (due to variations in specific plant resistance), plant size, and maturity. More mature plants are generally more resistant to herbicides and require higher dosage rates for a comparable level of control. Useful dosage rates can best be expressed in relation to active ingredient dosage rates and generally correspond to at least about 1 gallon active ingredient per acre, preferably at least about 10 gallons per acre, and more preferably at least about 50 gallons per acre. Dosage rates of about 10–100 gallons per acre are generally adequate to control most weeds and brush prevalent in field crop areas. The composition is usually applied once or twice to the unwanted vegetation. However, more frequent applications can be carried out to control more resilient vegetation. The phytotoxic effect of the treatment is observed usually between 1–7 days. Phytotoxicity measurements can be recorded using a ten-point scale, with zero indicating no visible phytotoxic effects and ten indicating death and total brown-down. Scale 0–10 indicates 0 (no death), 10, 20, 30, 40, 50, 60, 70, 80, 90, 100% (total death), respectively.

Another embodiment of the subject method is to apply the composition to the rhizosphere in an area containing unwanted vegetation, particularly non-woody vegetation.

The subject method can employ the compositions of this invention, along with sequential treatments with other phytotoxicants, fertilizers, and the like for maximum effect. For example, the field could be sprayed with a composition of this invention either before or after being treated with fertilizers, other phytotoxicants, and the like. The compositions of this invention can also be admixed with other materials, e.g., fertilizers, other phytotoxicants, etc., and can be applied in a single application.

As noted above, the subject method can be used to control weeds selectively or non-selectively. When selective, the method kills weeds without harming the desired crop, when non-selective, the method kills all vegetation. Selectivity can also be achieved mechanically by spray placement, a method of spraying only the target vegetation and not the crop plants. For example, a limited selectivity in crops such as cotton, soybeans, sugarcane, and like crops can be obtained by directing the spraying of a composition of this invention at a selected concentration on vegetation around the base of such plants with minimal spray contact with the leafy portions of such crop plants. The directed spraying can be done with or without a protective device to prevent contact of the spray with the leaves of such crop plants.

These methods are best illustrated by the preferred embodiments set forth below. One aspect of this invention is a method of controlling weeds, for example by inhibiting weed growth, which involves applying a composition of this invention to a weed at a herbicidally-effective level. Application methods include ground, aerial, chemigation, surface, soil incorporation, preplant, preemergent, postemergent, and the like, depending on the conditions of the weather, the type of plant, the time of year, and other factors known to those of skill in the art. Preferably, the composition is applied above ground to the surfaces of a growing plant such as the leaves, stem, blossoms and exposed roots. One application is generally enough, but more than one application may be made to obtain the desired results.

An exemplary method for controlling weeds comprises applying (such as by spraying) to a plant part of the weed, an herbicidally effective amount of a composition comprising an agriculturally-acceptable carrier in combination with a compound of Formula (I). This can be accomplished by contacting a plant part of said weed with the composition, where this part is preferably foliage or a root. In addition, another aspect of the invention involves translocation from a first plant part to a second plant part, which is typically from one plant cell to another plant cell. Translocation can also occur from a first plant part, such as the foliage of the weed to a second plant part, which is typically a root. The methods described herein are useful for killing weeds, or clearing an area of unwanted vegetation, where unwanted vegetation may include weeds or other plants, crops or flowers, etc., whose removal is desired.

There are numerous ways to minimize potential damage to the desired vegetation such as agricultural crops. For example, the methods described herein can be conducted prior to planting crops in an area containing weeds, or the application method can be performed selectively to the weeds in a given area as compared to agricultural or ornamental vegetation in the same area.

The active compounds of the herbicides of the present invention preferably are biorational chemicals that qualify for the US EPA Biorational Program.

The subject method effectively controls dry-land vegetation, including varieties of grasses, broad leafs, and succulents ranging from crabgrass, to varieties of forest trees, including broad leafs and conifers.

The subject method effectively controls dry-land vegetation, including varieties of grasses, broad leafs, and succulents ranging from crabgrass, to varieties of forest trees, including broad leafs and conifers. For example, common annual weeds include barley, barnyard grass, black nightshade, broadleaf signal grass, burcumber, chickweed, cocklebur, common ragweed, crabgrass, field pennycress, rough fleabane, foxtail, giant ragweed, goose grass, groundcherry, hemp sesbarria, henbit, jungle rice, kochia, lambs quarters, mare's tail/horseweed, morning-glory spp., mustard, fall and Texas panicum, palma amaranth, Pennsylvania smartweed, pigweed spp., prickly sida (teaweed), red rice, rye, seedling johnson grass, shattercone, shepherd's purse, sicklepod, sprangletop, sunflower, velvet leaf, volunteer corn, common and tall waterhemp, wheat, wild proso millet, witchgrass, wolly cupgrass; and common perennial weeds including Canada thistle, common milkweed, field bindweed, hemp dogbane, nutsedge spp., quackgrass, red vine, rhizone johnson grass, tall fescue, trumpet creeper, swamp smartweed and wisteria mukly. Star Thistle, Poison Oak, and Ivy are also weeds suited for treatment by the invention. Other annual and perennial weeds not listed here or described in the Examples, but known to those of ordinary skill in the art, would be suitable as targets by the composition of the present invention.

The subject method is also used to control aquatic vegetation. Excessive growth by aquatic vegetation diminishes the habitat for fish, although it initially increases shelter for smaller or younger fish. The flow of water through a system may be impeded, disrupting water delivery for human consumption or for irrigation. Other aquatic activities, such as boating and swimming, or transportation, may be curtailed. The subject method is used to control aquatic weeds, such as immersed aquatic weeds (cattails, bulrushes and arrowheads), submersed aquatic weeds (pondweeds, coontails and watermifoils), floating aquatic weeds (duckweeds, water hyacinth, waterlettuce, waterfems and waterlilies), and algae (watemet, pithophora and chara).

The application of herbicidal compositions to aquatic plants is usually carried out by spraying the compositions on the aquatic plants in the area where control of the aquatic plants is desired. Granules or larger-size pellets of clay and other materials impregnated with the subject compositions, can be applied to treat the water surface, the total water volume, the bottom 1 to 3-foot layer of water, or the bottom soil surface. Slow-release granules or pellets designed to release the subject composition in small amounts over an extended period in the water can also be used in treating aquatic weeds and aquatic pests.

The subject method is useful for control of weeds between cropping seasons, for the renovation of stale seed beds, and the like.

The subject method is useful in minimum-tillage methods of crop culture. For example, in those instances where it is desirable to plant a sodded or otherwise vegetated acreage with an agricultural crop without plowing or otherwise mechanically preparing a seed bed, the crop seed can be drill planted in combination with a prior or subsequent application of a composition of this invention to kill undesired growing vegetation provided that the composition is applied before the emergence of the crop plant.

The subject method is also useful in sod (turf, alfalfa, pasture, etc.) renovation or conversion procedures. For example, in situations where a sod or parts thereof has become overgrown with undesirable plant species, the plants in said area can be sprayed with the subject composition to control all growing plants, and from about 2 to 24 hours later depending upon weather conditions etc., the desired species can be seeded into the dying vegetation. In an alternate method of sod renovation, the area can be seeded and immediately sprayed with a composition of this invention. In either method, the seeds fall among the vegetation and as the sprayed plants wither and die, they act as a mulch and moisture-retaining layer in which the seeds can germinate. Seeds which are in the soil can germinate and grow without any apparent effects from the spraying of the unwanted plants prior to the time that the seed actually germinates.

The subject method can be used in agricultural and industrial sites. The industrial sites include roadsides, ditch banks, irrigation canals, fence lines, recreational areas, railroad embankments, and power lines. The subject methods remove undesirable plants that might cause damage, present fire hazards, or impede work crews. They also reduce costs of labor for mowing.

Article of Manufacture

Use of herbicides and other pesticides is regulated in the United States by the Environmental Protection Agency (EPA) under authority of the Federal Insecticide, Fungicide and Rodenticide Act (FIFRA). Tolerance for residues of pesticides in agricultural commodities are established by the (EPA) and enforced by the Food and Drug Administration (FDA) under authority of the Federal Food, Drug and Cosmetic Act (FD&C Act).

This regulatory environment leads to another aspect of this invention, which is an article of manufacture. In this aspect a herbicidally active compound represented by Formula (I) or (II), as defined above, is combined with an agriculturally-acceptable carrier in a container that will be suitable for storing the composition for its shelf life. Associated with the container is printed labeling providing instructions for using the composition for herbicidal purposes in accordance with the treatment method set forth herein. The container may have associated with it a delivery device that allows the composition to be applied to the weeds to be treated. For liquid compositions this is generally a hand-operated, motorized or pressurized pressure-driven sprayer. The container may be made of any suitable material such as a polymer, glass, metal, or the like. Usually, the labeling is associated with the container by being adhered to the container, or accompanying the container in a package sold to the user. Such label may indicate that the composition is approved for use as an herbicide. The instructions will spell out the type of plant for which the herbicidal composition is to be used, the application method, the rate of application, dilution requirements, use precautions, and the like.

EXAMPLES

| Abbreviations | |
|---|---|
| AC | Active Compound |
| T20 | TWEEN ® 20 |
| T-SP190 | TRITON ® SP190 (Union Carbide, Santa Ana, CA) |

Example 1

Experimental Field Trials I

This example provides an exemplary protocol to evaluate weed control following application of a herbicidal composition of this invention in comparison to other known herbicidal compositions or controls.

The location chosen should have a range of weeds including broadleaf weeds and grasses. An example of a suitable location is a pasture of the Armstrong Field Complex of the University of California, Davis, administered by the faculty of the Department of Plan Pathology is a useful test field. Monocots and dicots are generally present with an abundance of Shepherd's Purse (*Capsella bursa-pastoris* (l.) Medikus).

The duration of the study is one application followed by a time course evaluation (24 hours and 72 days).
Experimental Design (I) Treatments: Compositions comprising 1% by weight and 5% by weight of the active compound are applied to a plot of land and compared to other compositions. Suitable treatments for testing are listed below, including negative and positive controls.

(1) 1% AC and 0.5% T-SP190

(2) 5% AC and 0.6% T-SP190

(3) 0.5% T-SP190 (formula blank control)

(4) ROUNDUP®, at label rates (5) Control (negative-no treatment).

(II) Plot Design: The weeds used in this study are naturally occurring broadleaf and grasses (monocotyledons ["monocots"] and dicotyledons ["dicots"]), such as those found at the Armstrong pasture site at UC Davis. The criterion for selecting the plot is that there has been no previous weed control activity (physical or chemical) on the pasture. A plot 2 by 5 meters is marked off and divided into 10 equal areas. Each 1–2 meter area is flagged with two replications per treatment at the desired rate. Treatments are coded in a blind manner and are randomly assigned to treatment cells. Each formulation would be assigned a random number for blinding.

(III) Concentration/Mixing Instructions: Positive controls are sprayed with ROUNDUP® only solution per label instructions (1.50 oz./gallon). This represents a 1/85 dilution. 10.6 millimeters of ROUNDUP® are placed in a 1 liter bottle filled with 890 mls of water and shaken vigorously.

The two concentrations of an AC of Formula (I) or (II) are mixed in a similar manner. The 1% composition is prepared by placing 9.0 g of the AC and 1.80 g of T-SP190 in a 1 liter bottle and filled with 889 mls of water and shaken vigorously. The 5% is prepared by placing 45.0 g of the AC and 5.40 g of T-SP190 in a 1 liter bottle and filled with 850 mls of water and shaken vigorously.

The formula blank control is mixed as follows. The solution is prepared by placing 5.40 g of T-SP190 in a 1 liter bottle filling with 895 mls of water and shaking vigorously.

(IV) Method of Application: The treatments are applied by securing a standard wide spray nozzle to the formulae bottles, and spraying dedicated plots with assigned bottles. Treatments are sprayed separately, one trial plot at a time in order to minimize spraying errors due to drift.

(V) Observation Methods: Pretreatment: Photographs of the experimental plot for each treatment area are taken with a 35 mm YASHICA 230 AF camera with Kodak Royal Gold 400 speed color print film.

Post-treatment: Visual observations are made at 24 hours. Photographs are taken of the experimental plots for each treatment areas at 72 hours post treatment with the same camera used for pretreatment photographic documentation.

Trial Observations

Post-treatment at 24 hours. Any remarkable observations are recorded.

Post-treatment at 72 hours. Each treatment replicate is scored on a scale from 1 to 5. The scale represents the following stages of herbicidal efficacy:

1=No visible effect
2=Slightly mild phytotoxicity (some desiccation)
3=Strong phytotoxicity (desiccation and epinasty)
4=Profound phytotoxicity (strong desiccation and epinasty)
5=Death Replicate treatment ratings are conducted, recorded, and analyzed.

Example 2

Experimental Field Trials II

This example provides a second exemplary protocol to evaluate weed control following application of one herbicidal composition of this invention in comparison to other known herbicidal compositions or controls.

An exemplary location of the study is in the Armstrong Field Complex at the University of California, Davis as described in Example 1. This site contains monocots and dicots including broadleaf and grasses.

The duration of the study is one application followed by a time course evaluation at 24 hours and 40 hours.

Experimental Design (I) Treatments: Compositions comprising 1% to 5% by weight of the active compound are applied to a plot and compared to other compositions. The six treatments to be evaluated against weeds for herbicidal activity are listed below:

(1) 0.6% T-SP190 (Formula Blank)
(2) ROUNDUP® per labe-1.5 oz/128 oz approximately 5.86 mls
(3) 1.0% AC and 0.10% T-SP190
(4) 3.0% AC and 0.30% T-SP190
(5) 5.0% AC and 0.50% T-SP190
(6) Negative control-no treatment.

(II) Plot Design: The weeds used in this study are naturally occurring broadleaf and grasses, such as monocots and dicots. The criterion for selecting the plot is the fact that there has been no previous weed control activity (physical or chemical) on the weed plants. A plot 1 meter by 6 meters is marked off and divided into 6 equal areas. Each meter area is flagged per assigned treatment. Treatments are coded in a blind manner and are randomly assigned to the treatment plot at time of spray. Each will have a randomly assigned number for blinding.

(III) Concentration/Mixing Instructions: Positive control (Treatment #2) is sprayed with ROUNDUP® only solution per label instructions (1.50 oz./128 gallon). 5.86 mls of ROUNDUP® is placed in a 1 liter bottle, then 494 mls of water is added and the mixture shaken vigorously.

Formula blank (Treatment #1) is prepared by placing 3.0 g of T-SP190 into a 1 liter bottle, then 497 mls of water added and shaken vigorously.

Exemplary AC treatments are prepared as follows: Treatment #3 is prepared by placing 1.0 g of AC and 0.10 g of T-SP190 into a 1 liter bottle, then 499 mls of water added and shaken vigorously. Treatment #4 is prepared by placing 3.0 g of AC and 0.30 g of T-SP190 into a 1 liter bottle, then 497 g of water added and shaken vigorously. Treatment #5 is prepared by placing 5.0 g of AC and 0.50 g of T-SP190 into a 1 liter bottle and adding 494 mls of water and shaken vigorously.

(IV) Method of Application: The treatments are applied by securing a standard wide spray nozzle to the formula treatment bottles and then spraying dedicated plots with randomly assigned treatments. Treatments are sprayed separately, one trial plot at a time in order to minimize spraying errors due to drift.

(V) Observation Methods: Pretreatment: Photographs of the experimental plot for each treatment area are taken with a 35 mm YASHICA 230 AF camera with Kodak Royal Gold 400 speed color print film.

Post-treatment: Visual and photographic observations are made at 24 hours and 40 hours post-treatment with same camera used for pretreatment documentation.

Trial Observations

Post-treatment at 24 hours and at 40 hours. Each treatment is scored on a scale that ranged from 1 to 5. The scale represents the following degree of herbicidal efficacy: Post-treatment at 72 hours.

1=No visible effect
2=Slightly mild phytotoxicity (some desiccation)
3=Strong phytotoxicity (desiccation and epinasty)
4=Profound phytotoxicity (strong desiccation and epinasty)
5=Death Example 3

Summary Results

TABLE II

| Herbicidal Efficacy | |
| --- | --- |
| Active Compound | Phytotoxicity |
| cinnamyl acetate[1, 2] | strong |

[1]Naturally occurring compound
[2]GRAS ("Generally Recognized As Safe") compound Phytotoxicity was rated qualitatively based upon field data from field trials using plots of mixed weed species, both broadleaf weeds ("BLW") and grass weeds ("GW"), and from laboratory experiments using tobacco plants, strawberry plants or turfgrass.

The types of BLW and GW tested included purslane speedwell, henbit, shepherd's purse, common chickweed, knotweed, wild stem filaree, fiddleneck, miner's lettuce, red maids, velvetleaf, lambs quarters, groundcherry, prostrate pigweed, hairy nightshade, black nightshade, Poa, perennial ryegrass, tall fescue, annual bluegrass, wild barley, barnyard grass, jungle rice and crabgrass.

Based on the experiments conducted, the types of symptoms observed on plants treated with the compound listed above, were consistent with those of a contact herbicide.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for controlling weeds, which method comprises applying to a plant part of the weed an herbicidally effective amount of a composition comprising an agriculturally-acceptable carrier in combination with a compound of Formula (I):

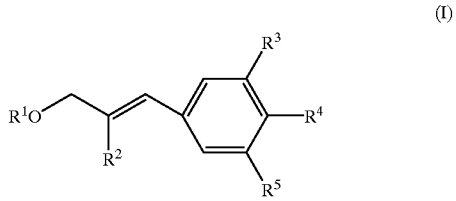

(I)

wherein $R^1$ is alkylcarbonyl or arylcarbonyl; $R^2$ is alkyl or H; $R^3$ is H, OH or alkoxy; $R^4$ is H or OH; and $R^5$ is H, OH or alkoxy.

2. The method of claim 1 wherein $R^1$ is $C_{1-5}$alkylcarbonyl or arylcarbonyl; $R^2$ is $C_{1-6}$alkyl or H; $R^3$ is H, OH or $C_{1-4}$alkoxy; $R^4$ is H or OH; and $R^5$ is H, OH or $C_{1-4}$alkoxy.

3. The method of claim 2 wherein $R^1$ is methylcarbonyl or phenylcarbonyl; $R^2$ is n-propyl, n-hexyl, amyl or H; $R^3$ substituent is H or methoxy; $R^4$ is H; $R^5$ is H or methoxy.

4. The method of claim 1 wherein $R^1$ is methylcarbonyl.

5. The method of claim 1 wherein one or more of $R^2$, $R^3$, $R^4$ and $R^5$ are H.

6. The method of claim 1 wherein said compound is selected from the group consisting of cinnamyl acetate, cinnamyl benzoate, α-propyl cinnamyl benzoate, α-amyl cinnamyl acetate, α-hexyl cinnamyl benzoate, coniferyl acetate, coniferyl benzoate, α-amyl coniferyl acetate, sinapyl acetate and sinapyl benzoate.

7. The method of claim 6 wherein said compound is cinnamyl acetate.

8. The method of claim 1 wherein the weeds are broadleaf weeds or grasses.

9. The method of claim 1 wherein the agriculturally-acceptable carrier comprises a surfactant.

10. The method of claim 9 wherein the surfactant is a polyoxyethylated sorbitol fatty acid ester.

11. The method of claim 9 wherein the surfactant is a polyethyleneglycol ether.

12. The method of to claim 1 wherein said plant part is foliage.

13. The method of to claim 1 wherein said plant part is a root.

14. The method of claim 1 wherein said applying to a plant part occurs prior to planting crops in an area Containing said weeds.

15. The method of claim 1 wherein said applying to a plant part is performed selectively to said weeds in an area as compared to agricultural or ornamental vegetation in said area.

16. The method of claim 1 wherein said weeds are aquatic weeds.

17. The method of claim 1 wherein the composition is applied to an area of weeds at a rate of about 0.5 pounds to about 6 pounds per square foot.

18. The method of claim 1 wherein the composition is applied by spraying.

19. The method of claim 1 wherein the compound is a naturally-occurring compound.

* * * * *